(12) United States Patent
Lal et al.

(10) Patent No.: US 6,326,207 B1
(45) Date of Patent: Dec. 4, 2001

(54) HUMAN SODIUM-DEPENDENT PHOSPHATE COTRANSPORTER

(75) Inventors: Preeti Lal, Sunnyvale; Olga Bandman, Mountain View, both of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/391,958

(22) Filed: Sep. 8, 1999

Related U.S. Application Data

(62) Division of application No. 08/805,118, filed on Feb. 24, 1997, now Pat. No. 5,985,604.

(51) Int. Cl.[7] .......................... C07K 14/00; A61K 38/00; G01N 33/00
(52) U.S. Cl. ................................ 436/86; 514/12; 530/350
(58) Field of Search .............................. 530/350; 514/12; 436/86

(56) References Cited

U.S. PATENT DOCUMENTS 5,872,237 * 2/1999 Feder et al. ...................... 536/23.5

FOREIGN PATENT DOCUMENTS

WO 98/14466   4/1998  (WO) .

OTHER PUBLICATIONS

Gasparini, Direct Submission, 1997, GenBank Accession No. HSZ83953.*
Hartmann, C.M., et al., "Structure of murine and human renal type II Na+–phosphate cotransporter genes (Npt2 and NPT2)." *Proc.Natl.Acad.Sci.USA* (1996) 93:7409–7414.
Glinn, M., et al., "Characterization of Na(+)–dependent phosphate uptake in cultured fetal rat cortical neurons." *J.Neurochem.* (1995) 65:2358–2365.
Tenenhouse, H.S., et al., "Effect of phosphonoformic acid, dietary phosphate and the Hyp mutation on kinetically distinct phosphate transport processes in mouse kidney." *Biochim.Biophys.Acta* (1989) 984(2):207–213.
Fulceri, R., et al., "Physiological concentrations of inorganic phosphate affect MgATP–dependent Ca2+ storage and inositol trisphosphate–induced Ca2+ efflux in microsomal vesicles from non–hepatic cells." *Biochem.J.* (1993) 289 (Pt 1):299–306.
Chong, S.S., et al., "Molecular Cloning of the cDNA Encoding a Human Renal Sodium Phosphate Transport Protein and Its Assignment to Chromosome 6p21.3–p23." *Genomics* (1993) 18:355–359. (GI 450532).
Miyamoto, K., et al., "Cloning and functional expression of a Na+–dependent phosphate co–transporter from human kidney: cDNA cloning and functional expression." *Biochem.J.* (1995) 305:81–85.

Ni B., et al., "Regional expression and cellular localization of the Na (+)–dependent inorganic phosphate cotransporter of rat brain", *Journal of Neuroscience*, 15 (8): 5789–5799 (1995).
Gupta, A., et al., "Phosphate transport in osteoclasts: a functional and immunochemical characterization." *Kidney Int.* (1996) 49:968–974.
Kos, C.H., et al., "Localization of a renal sodium–phosphate cotransporter gene to human chromosome 5q35." *Genomics* (1994) 19:176–177.
Chong, S.S., et al. (GI 450532), GenBank Sequence Database (Accession X71355), National Center for Biotechnology Information, National Library of Medicine, Bethesda, Maryland, 20894.
Chong, S.S., et al. (GI 450531), GenBank Sequence Database (Accession X71355), National Center for Biotechnology Information, National Library of Medicine, Bethesda, Maryland, 20894. (GI 450532).
Ni, B., et al. (GI 507415), GenBank Sequence Database (Accession U07609), National Center for Biotechnology Information, National Library of Medicine, Bethesda, Maryland, 20894.
Ni, B., et al. (GI 507414), GenBank Sequence Database (Accession U07609), National Center for Biotechnology Information, National Library of Medicine, Bethesda, Maryland, 20894. (GI 507415).
Ni, B., et al., "Cloning and expression of a cDNA encoding a brain–specific Na(+)–dependent inorganic phosphate cotransporter." *Proc.Natl.Acad.Sci.USA* (1994) 91(12):5607–5611. (GI 507415).
Messing, J., et al., "A system for shotgun DNA sequencing." *Nucleic Acids Res.* (1981) 9:309–321.
Gasparini, p., "EMBL Database Entry HSZ83953," Accession No. Z83953, XP002069029, Jan. 16, 1997.

(List continued on next page.)

*Primary Examiner*—Rebecca E. Prouty
*Assistant Examiner*—David J. Steadman
(74) *Attorney, Agent, or Firm*—Incyte Genomics, Inc

(57) ABSTRACT

The present invention provides a human sodium-dependent phosphate cotransporter (NAPTR) and polynucleotides which identify and encode NAPTR. The invention also provides genetically engineered expression vectors and host cells comprising the nucleic acid sequences encoding NAPTR and a method for producing NAPTR. The invention also provides for agonists, antibodies, or antagonists specifically for NAPTR. Additionally, the invention provides for the use of antisense molecules to polynucleotides encoding NAPTR for the treatment of diseases associated with the expression of NAPTR. The invention also provides diagnostic assays which utilize the polynucleotide, or fragments or the complement thereof, and antibodies specifically binding NAPTR. The invention also provides a method for treating disorders associated with decreased phosphate levels by administering NAPTR and a method for treating disorders associated with increased phosphate levels by administering antagonists to NAPTR.

6 Claims, 8 Drawing Sheets

OTHER PUBLICATIONS

Hui, Li, et al., "Molecular cloning of two rat Na+/Pi cotransporters: evidence for differential tissue expression of transcripts," *Cellular and Molecular Biology Research,* vol. 41, No. 5, pp. 451–460, XP002069025, 1995.

Samuel S. Chong, et al., "Cloning, genetic maping, and expression analysis of a mouse renal sodium–dependent phosphate cotransporter," *American Journal of Physiology: Renal, Fluid and Electrolyte Physiology,* vol. 37, No. 6, pp. F1038–F1045, XP002069026, Jun. 1995.

Ken–Ichi Miyamoto, et al., "Cloning and functional expression of a Na+–dependent phosphate co–transporter from human kidney: cDNA cloning and functional expression," *Biochemical Journal,* vol. 305, No. 1, pp. 81–85, XP002069027, Jan. 1, 1995.

Ruddy, D.A., et al., "A 1.1 megabase transcript map of the human hereditary hemochromatosis locus," *EMBL Database Entry HSU90545,* XP002069031, Accession No. U90545, Jun. 3, 1997.

Ruddy, D.A., et al., EMBL Database entry 000476, Accession No. 00476, XP002069030, Jul. 1, 1997.

Accession D28532 "HumanmRNA for renal Na+–dependent phosphate cotransporter, complete Cds." Submitted by K. Miyamoto (Jun. 18, 1996).

Accession H60468 "yr42a05.r1 Homo sapianscDNA clone 207920 5' similar to SP:S27951" Submitted by R.K. Wilson (Oct. 6, 1995).

* cited by examiner

```
              9           18          27          36          45          54
5' AGA ACG GTG AGG ATG ACC GAC GTA TAG GCG AGA GCC TAG GTA CGC CAT GCC AGG 63          72          81          90          99         108
   TCA CCG GTC CGG CAA TTC CCG GGT CGA CCC ACG CGT CCG CTT GGA GGG ACG CTG 117         126         135         144         153         162
   GGT TCA ACT TGA AGC CCT TCC ACA GAC ATT AAG TCG GTG AAA ACC ATT CAC TAG 171         180         189         198         207         216
   GAG AGG AGA AAC ACA ATG GCC ACC AAG ACA GAG TTG AGT CCC ACA GCA AGG GAG 225         234         243         252         261         270
   AGC AAG AAC GCA CAA GAT ATG CAA GTG GAT GAG ACA CTG ATC CCC AGG AAA GTT
                                    M   Q   V   D   E   T   L   I   P   R   K   V 279         288         297         306         315         324
   CCA AGT TTA TGT TCT GCT CGC TAT GGA ATA GCC CTC GTC TTA CAT TTC TGC AAT
    P   S   L   C   S   A   R   Y   G   I   A   L   V   L   H   F   C   N 333         342         351         360         369         378
   TTC ACA ACG ATA GCA CAA AAT GTC ATC ATG AAC ATC ACC ATG GTA GCC ATG GTC
    F   T   T   I   A   Q   N   V   I   M   N   I   T   M   V   A   M   V 387         396         405         414         423         432
   AAC AGC ACA AGC CCT CAA TCC CAG CTC AAT GAT TCC TCT GAG GTG CTG CCT GTT
    N   S   T   S   P   Q   S   Q   L   N   D   S   S   E   V   L   P   V 441         450         459         468         477         486
   GAC TCA TTT GGT GGC CTA AGT AAA GCC CCA AAG AGT CTT CCT GCA AAG TCC TCA
    D   S   F   G   G   L   S   K   A   P   K   S   L   P   A   K   S   S 495         504         513         522         531         540
   ATA CTT GGG GGT CAG TTT GCA ATT TGG GAA AGG TGG GGC CCT CCA CAA GAA CGA
    I   L   G   G   Q   F   A   I   W   E   R   W   G   P   P   Q   E   R 549         558         567         576         585         594
   AGC AGA CTC TGC AGC ATT GCT TTA TCA GGA ATG TTA CTG GGA TGC TTT ACT GCC
    S   R   L   C   S   I   A   L   S   G   M   L   L   G   C   F   T   A 603         612         621         630         639         648
   ATC CTC ATA GGT GGC TTC ATT AGT GAA ACC CTT GGG TGG CCC TTT GTC TTC TAT
    I   L   I   G   G   F   I   S   E   T   L   G   W   P   F   V   F   Y 657         666         675         684         693         702
   ATC TTT GGA GGT GTT GGC TGT GTC TGC TGC CTT CTC TGG TTT GTT GTG ATT TAT
    I   F   G   G   V   G   C   V   C   C   L   L   W   F   V   V   I   Y
```

FIGURE 1A

```
        711           720           729           738           747           756
GAT GAC CCC GTT TCC TAT CCA TGG ATA AGC ACC TCA GAA AAA GAA TAC ATC ATA
 D   D   P   V   S   Y   P   W   I   S   T   S   E   K   E   Y   I   I 765           774           783           792           801           810
TCC TCC TTG AAA CAA CAG GTC GGG TCT TCT AAG CAG CCT CTT CCC ATC AAA GCT
 S   S   L   K   Q   Q   V   G   S   S   K   Q   P   L   P   I   K   A 819           828           837           846           855           864
ATG CTC AGA TCT CTA CCC ATT TGG TCC ATA TGT TTA GGC TGT TTC AGC CAT CAA
 M   L   R   S   L   P   I   W   S   I   C   L   G   C   F   S   H   Q 873           882           891           900           909           918
TGG TTA GTT AGC ACA ATG GTT GTA TAC ATA CCA ACT TAC ATC AGC TCT GTG TAC
 W   L   V   S   T   M   V   V   Y   I   P   T   Y   I   S   S   V   Y 927           936           945           954           963           972
CAT GTT AAC ATC AGA GAC AAT GGA CTT CTA TCT GCC CTT CCT TTT ATT GTT GCC
 H   V   N   I   R   D   N   G   L   L   S   A   L   P   F   I   V   A 981           990           999          1008          1017          1026
TGG GTC ATA GGC ATG GTG GGA GGC TAT CTG GCA GAT TTC CTT CTA ACC AAA AAG
 W   V   I   G   M   V   G   G   Y   L   A   D   F   L   L   T   K   K 1035          1044          1053          1062          1071          1080
TTT AGA CTC ATC ACT GTG AGG AAA ATT GCC ACA ATT TTA GGA AGT CTC CCC TCT
 F   R   L   I   T   V   R   K   I   A   T   I   L   G   S   L   P   S 1089          1098          1107          1116          1125          1134
TCA GCA CTC ATT GTG TCT CTG CCT TAC CTC AAT TCC GGC TAT ATC ACA GCA ACT
 S   A   L   I   V   S   L   P   Y   L   N   S   G   Y   I   T   A   T 1143          1152          1161          1170          1179          1188
GCC TTG CTG ACG CTC TCT TGC GGA TTA AGC ACA TTG TGT CAG TCA GGA ATT TAT
 A   L   L   T   L   S   C   G   L   S   T   L   C   Q   S   G   I   Y 1197          1206          1215          1224          1233          1242
ATC AAT GTC TTA GAT ATT GCT CCA AGG TAT TCC AGT TTT CTC ATG GGA GCA TCA
 I   N   V   L   D   I   A   P   R   Y   S   S   F   L   M   G   A   S 1251          1260          1269          1278          1287          1296
AGA GGA TTT TCG AGC ATA GCA CCT GTC ATT GTA CCC ACT GTC AGC GGA TTT CTT
 R   G   F   S   S   I   A   P   V   I   V   P   T   V   S   G   F   L 1305          1314          1323          1332          1341          1350
CTT AGT CAG GAC CCT GAG TTT GGG TGG AGG AAT GTC TTC TTC TTG CTG TTT GCC
 L   S   Q   D   P   E   F   G   W   R   N   V   F   F   L   L   F   A 1359          1368          1377          1386          1395          1404
GTT AAC CTG TTA GGA CTA CTC TTC TAC CTC ATA TTT GGA GAA GCA GAT GTC CAA
 V   N   L   L   G   L   L   F   Y   L   I   F   G   E   A   D   V   Q
```

FIGURE 1B

```
        1413          1422          1431          1440          1449          1458
GAA TGG GCT AAA GAG AGA AAA CTC ACT CGT TTA TGA AGT TAT CCC ACC TTG GAT
 E   W   A   K   E   R   K   L   T   R   L 1467          1476          1485          1494          1503          1512
GGA AAA GTC ATT AGG CAC CGT ATT GCA TAA AAT AGA AGG CTT CCG TGA TGA AAA 1521          1530          1539          1548          1557          1566
TAC CAG TGA AAA GAT TTT TTT TTC CTG TGG CTC TTT TCA ATT ATG AGA TCA GTT 1575          1584          1593          1602          1611          1620
CAT TAT TTT ATT CAG ACT TTT TTT TGA GAG AAA TGT AAG ATG AAT AAA AAT TCA 1629          1638
AAT AAA ATG ATA ACT AAG AAT GC 3'
```

FIGURE 1C

```
  1  MQVDE- - - - - TLIPRKVPSL- - - - - - - - - - - - - - - - - - - - - - - - - - - - - - - - - - - - - - - - - - - - - - -  754412
  1  MQMDN- - - - - RLPPKKVPGF- - - - - - - - - - - - - - - - - - - - - - - - - - - - - - - - - - - - - - - - - - - - - - -  GI 450532
  1  MEFRQEEFRKLAGRLHRLLEKRQEGAETLELSADGR                                                                                      GI 507415

16  - - - - - - - - - - - - CSA- - - - - - RYGIALV- -LHFCNFTTIA                                                                754412
 16  - - - - - - - - - - - - CSF- - - - - - RYGLSFL- -VHCCNVIITA                                                                GI 450532
 41  PVTTHTRDPPVVDCTCFGLPRRYIIAIMSGLGFC- -ISFG                                                                                  GI 507415

36  QNVIMNITMVAMVNSTSPQSQLNDSSEVL- - - - - - - - - - - - - - -                                                                 754412
 36  QRACLNLTMVVMVNSTDPHGLPNTSTKKLLDNIKNPMYNW                                                                                   GI 450532
 79  IRCNLGVALVSMVNNSTTH- - - - RGGHVV- - - VQKAQFNW                                                                            GI 507415

65  - - - - - - - PVDSFGGLSKAPKSL- - -                                                                                         754412
 76  SPDIQGIILSSTSYGVIHIIQVPVGYEFSGIYSTKKMIGFAL                                                                                 GI 450532
112  DPETVGLIHGSFFWGYIVTQIPGGFICQKFAANRVFGFAI                                                                                   GI 507415

80  - - - - - - - - - - - - - - - - - - PAKSSILGGQF                                                                            754412
116  CLSSVLSLLIPPAAGIGVAWVVVCRAVQGAIAQGIVATAQF                                                                                  GI 450532
152  VATSTLNMLIPSAARVHYGCVIFVRILQGLVEGVTYPACH                                                                                   GI 507415

91  AIWERWGPPQEERSRLCSIALSGMLLGCFTAILIGGFISET                                                                                  754412
156  EIYVKWAPPLERGRLTSMSTSGFLLGPEIVLLVTGVICES                                                                                   GI 450532
192  GIWSKWAPPLERSRLATTAFCGSYAGAVVAMPLAGVLVQY                                                                                   GI 507415

131  LGWPFVFYIFGGVGCVCCLLWFVVIYDDPVSYPWISTSEK                                                                                   754412
196  LGWPMVFYIFGACGLLWFVLFYDDPKDHPCISISEK                                                                                       GI 450532
232  SGWSSVFYVYGSFGIFWYLFWLLVSYESPALHPSISEEER                                                                                   GI 507415

171  EYIISSLKQQV- - - - -GSSKQPLPIKAMLRSLPIWSICLGC                                                                               754412
236  EYITSSLVQQV- - - - - SISSRQSLPIKAILKSLPVWAISIGS                                                                             GI 450532
272  KYIEDAIGESAKLMNPVTKFNTPWRRFFTSMPVYALIVAN                                                                                   GI 507415
```

FIGURE 2A

```
207 FSHQWLVSTMVVYIPTYISSVYHVNIRDNGLLSALPFIVA          754412
272 FTFFWSHNIMTLYTPMFINSMLHVNIKENGFLSISLPYLFA         GI 450532
312 FCRSWTFYLLISQPAYFEEVFGFEISKVGLVSALPHLVM           GI 507415

247 WVIGMVGGYLADFLLTKK-FRLITVRKIATILGSLPSSAL          754412
312 WICGNLAGQLSDFFLFLTRNILSVIAVRKLFTAAGFLLPAIF        GI 450532
352 TIIVPIGGQIADFLRSRHIMSTTNVRKLMNCGGFGMEATL          GI 507415

286 IVSLPYLNSGYITATALLTLSCGLSTLCQSGIYINVLDIA          754412
352 GVCLPYLSSTFYSIVIFLILAGATGSFCLGGVFLINGLDIA         GI 450532
392 LLVVGIYSHSKGVAIS-FLVLAVGFSGFAISGFNVNHLDIA         GI 507415

326 PRYSSFLMGASRGFSSIAPVIVPTVSGFLLSQDPEFGWRN          754412
392 PRYFGFIKACSTLTGMIGGLIASTLTGLILKODPESAWFK          GI 450532
431 PRYASILMGISNGVGTLSGMVCPIIVGAMTKHKTREEWQY          GI 507415

366 VFFLLFAVNLLGLLFYLIFGEADVQEWAKERKLTR - - -          754412
432 TFILMAAINVTGLIFYLIVATAEIQDWAKEKQHTR - - -          GI 450532
471 VFLIASLVHYGGVIFYGVFASGEKQPWAEPEEMSEEKCGF          GI 507415

401 - - - - - - - - - - - - - - - - - - - - - - - - - - - - - - - - - - - - - - -    754412
467 - - - - - - - - - - - - - - - - - - - - - - - - - - - - - - - - - - - - - - -    GI 450532
511 VGHDQLAGSDESEMEDEVEPPGAPPAPPPSYGATHSTVQP          GI 507415

401 - - - - - - - - - - - L                           754412
467 - - - - - - - - - - - L                           GI 450532
551 PRPPPPVRDY                                        GI 507415
```

FIGURE 2B

HUMAN SODIUM-DEPENDENT PHOSPHATE COTRANSPORTER

This application is a divisional application of U.S. application Ser. No. 08/805,118, filed Feb. 24, 1997, now U.S. Pat. No. 5,985,604.

FIELD OF THE INVENTION

This invention relates to nucleic acid and amino acid sequences of a novel human sodium-dependent phosphate cotransporter and to the use of these sequences in the diagnosis, prevention, and treatment of diseases associated with increased or decreased phosphate levels.

BACKGROUND OF THE INVENTION

Phosphate is present in the plasma, intracellular fluid, cell membranes, collagen and bone tissue of mammals. It is a dynamic constituent of energy metabolism, an essential component of skeletal mineralization, a modulator of tissue concentrations of calcium, and plays a major role in renal excretion of $H^+$.

Phosphate homeostasis in mammals is a balance between intake, intestinal absorption, bone deposition/resorption, and renal excretion and resorption. An excess of phosphate reduces the circulating $Ca^{2+}$ levels, and a deficit results in decreases in erythrocyte ATP and 2,3-diphosphoglycerate and contributes to the pathology of osteomalacia, hypocalciuria, and rickets. Dietary phosphate is absorbed from the gastrointestinal tract in an active, energy-dependent process that is modified by hormones, vitamin D, $Ca^{2+}$, and $Al^{3+}$. Regulation of the serum concentration of phosphate is maintained through resorption by the sodium phosphate cotransport system, located in the proximal convoluted renal tubule. Local concentration of phosphate in specific tissue types, such as liver, bone, and brain, is modulated by sodium phosphate transport proteins located in these tissues. (Hartmann, C. et al. (1996) Proc. Natl. Acad. Sci. 93:7409–7414; Glinn, M. et al.(1995) J. Neurochem. 65:2358–2365).

Human NPT1, NPT2, $NaP_1$-3, and the X-linked hypophosphatemia (PEX) sodium phosphate transport proteins are found in the renal brush border membrane where they participate in renal tubular phosphate uptake. Although similar in function, these renal proteins differ in affinity, capacity, map to different chromosomal locations, and are differentially regulated by hormones and dietary phosphate (Tenenhouse, H. (1989) Biochem. Biophys. Acta 984: 207–213; Fulceri, R. (1993) Biochem. J. 289:299–306; Chong, S. et al. (1993) Genomics 18:355–359; Miyamoto, K. et al. (1995) Biochem. J. 305:81–85).

Sodium phosphate transport proteins in rat brain neurons regulate intracellular phosphate concentrations necessary for maintaining the phosphorylation potential of the cell. Physiological concentrations of phosphate enhance the ATP-dependent binding of $Ca^{2+}$ to brain microsomes, resulting in a larger intracellular pool of $Ca^{2+}$ released by inositol triphosphate. The expression of the brain specific sodium-dependent phosphate transporter, rBNPI, is developmentally regulated and is specific to neuron enriched regions of the adult rat brain. Avian osteoclasts express a sodium-dependent phosphate transporter regulated through integrin-mediated pathways in the presence of bone. This transporter is hypothesized to act in the transcellular movement of phosphate during active bone resorption (Ni, B. (1995) J. Neurosci. 15: 5789–5799; Gupta, A. (1996) Kidney Int. 46: 968–974).

By low stringency screening of a human kidney cortex cDNA library with a rabbit NaP1-1 cDNA, Chong et.al. (1993, supra) isolated a cDNA encoding a human sodium-dependent phosphate transport protein (NPT1). Localization of NPT1 to 6p23–p21.3 was found by Southern hybridization to HindIII-digested DNA from a human chromosome 6 somatic cell hybrid deletion panel. Fluorescence in situ hybridization maps NPT1 to 12p11 in the rabbit. This assignment agrees with the previously reported homology between rabbit chromosome 12 and human chromosome 6 (Kos, C. et al. (1994) Genomics 19: 176–177).

The discovery of proteins related to human renal sodium phosphate transport protein, and the polynucleotides encoding them, satisfies a need in the art by providing new compositions useful in diagnosis and treatment of diseases associated with increased or decreased phosphate levels.

SUMMARY OF THE INVENTION

The present invention features a novel human sodium-dependent phosphate cotransporter hereinafter designated NAPTR and characterized as having similarity to human renal sodium phosphate transport protein and rat brain-specific sodium-dependent inorganic phosphate cotransporter.

Accordingly, the invention features a substantially purified NAPTR having the amino acid sequence shown in SEQ ID NO: 1.

One aspect of the invention features isolated and substantially purified polynucleotides that encode NAPTR. In a particular aspect, the polynucleotide is the nucleotide sequence of SEQ ID NO:2.

The invention also relates to a polynucleotide sequence comprising the complement of SEQ ID NO:2 or variants thereof In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode NAPTR. The present invention also features antibodies which bind specifically to NAPTR, and pharmaceutical compositions comprising substantially purified NAPTR. The invention also features agonists and antagonists of NAPTR. The invention also features a method for treating disorders associated with decreased phosphate levels by administering NAPTR and a method for treating disorders associated with increased phosphate levels by administering an antagonist to NAPTR.

BRIEF DESCRIPTION OF THE FIGURES

FIGS. 1A, 1B, and 1C show the amino acid sequence (SEQ ID NO: 1) and nucleic acid sequence (SEQ ID NO:2) of NAPTR. The alignment was produced using MacDNASIS PRO™ software (Hitachi Software Engineering Co., Ltd., San Bruno, Calif.).

FIGS. 2A and 2B show the amino acid sequence alignments among NAPTR (SEQ ID NO: 1), human sodium phosphate transporter protein (GI 450532; SEQ ID NO:3), and rat brain-specific sodium-dependent inorganic phosphate cotransporter (GI 507415; SEQ ID NO:4). The alignment was produced using the multisequence alignment program of DNASTAR™ software (DNASTAR Inc, Madison Wis.).

DESCRIPTION OF THE INVENTION

Figure 3A:
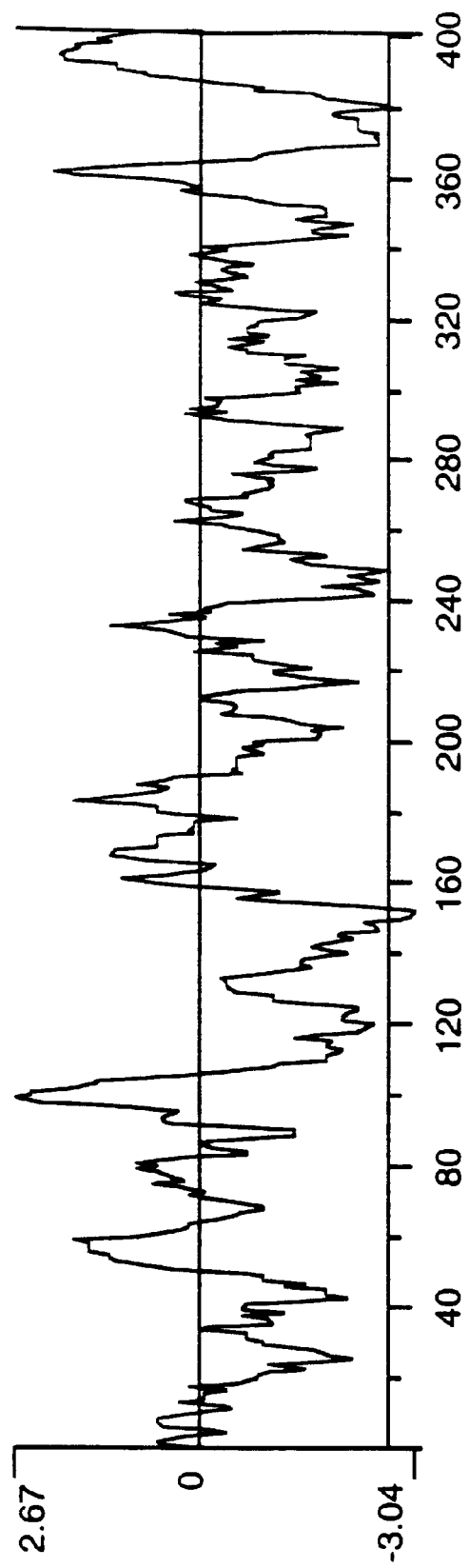
FIGS. 3A, 3B, and 3C show the hydrophobicity plots (MacDNASIS PRO software) for NAPTR, SEQ ID NO: 1, human sodium phosphate transporter protein, SEQ ID NO:3, and rat brain-specific sodium-dependent inorganic phosphate cotransporter, SEQ ID NO:4, respectively. The positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

NAPTR, as used herein, refers to the amino acid sequences of substantially purified NAPTR obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™(Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of NAPTR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic NAPTR, or any oligopeptide thereof, to induce a specific immune response in appropriate animals or cells and to bind with specific antibodies.

The term "agonist", as used herein, refers to a molecule which, when bound to NAPTR, causes a change in NAPTR which modulates the activity of NAPTR. Agonists may include proteins, nucleic acids, carbohydrates, or any other molecules which bind to NAPTR.

The terms "antagonist" or "inhibitor", as used herein, refer to a molecule which, when bound to NAPTR, blocks or modulates the biological or immunological activity of NAPTR. Antagonists and inhibitors may include proteins, nucleic acids, carbohydrates, or any other molecules which bind to NAPTR.

The term "modulate", as used herein, refers to a change or an alteration in the biological activity of NAPTR. Modulation may be an increase or a decrease in protein activity, a change in binding characteristics, or any other change in the biological, functional or immunological properties of NAPTR.

The term "mimetic", as used herein, refers to a molecule, the structure of which is developed from knowledge of the structure of NAPTR or portions thereof and, as such, is able to effect some or all of the actions of NAPTR-like molecules.

The term "derivative", as used herein, refers to the chemical modification of a nucleic acid encoding NAPTR or the encoded NAPTR. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human NAPTR and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding NAPTR or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding NAPTR in a sample and thereby correlates with expression of the transcript from the polynucleotide encoding the protein.

"Alterations" in the polynucleotide of SEQ ID NO:2, as used herein, comprise any alteration in the sequence of polynucleotides encoding NAPTR including deletions, insertions, and point mutations that may be detected using hybridization assays. Included within this definition is the detection of alterations to the genomic DNA sequence which encodes NAPTR (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding NAPTR (e.g., using fluorescent in situ hybridization [FISH] to metaphase chromosomes spreads).

As used herein, the term "antibody" refers to intact molecules as well as fragments thereof, such as Fa, $F(ab')_2$, and Fv, which are capable of binding the epitopic determinant. Antibodies that bind NAPTR polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human sodium-dependent phosphate cotransporter, NAPTR, the polynucleotides encoding NAPTR, and the use of these compositions for the diagnosis, prevention, or treatment of disorders associated with increased or decreased phosphate levels.

Nucleic acids encoding the human NAPTR of the present invention were first identified in Incyte Clone 754412 from the brain tumor cDNA library (BRAITUT02) through a computer-generated search for amino acid sequence alignments. A consensus sequence, SEQ ID NO:2, was derived from the extension of the nucleic acid sequence of Incyte Clone 754412.est (BRAITUT02).

Figure 3B:
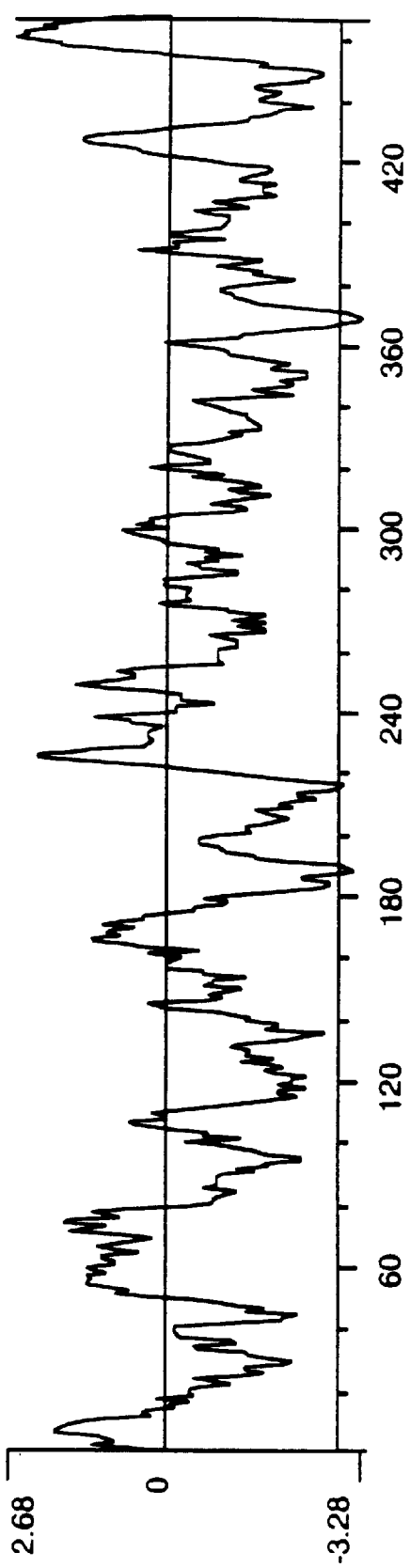
Figure 3C:
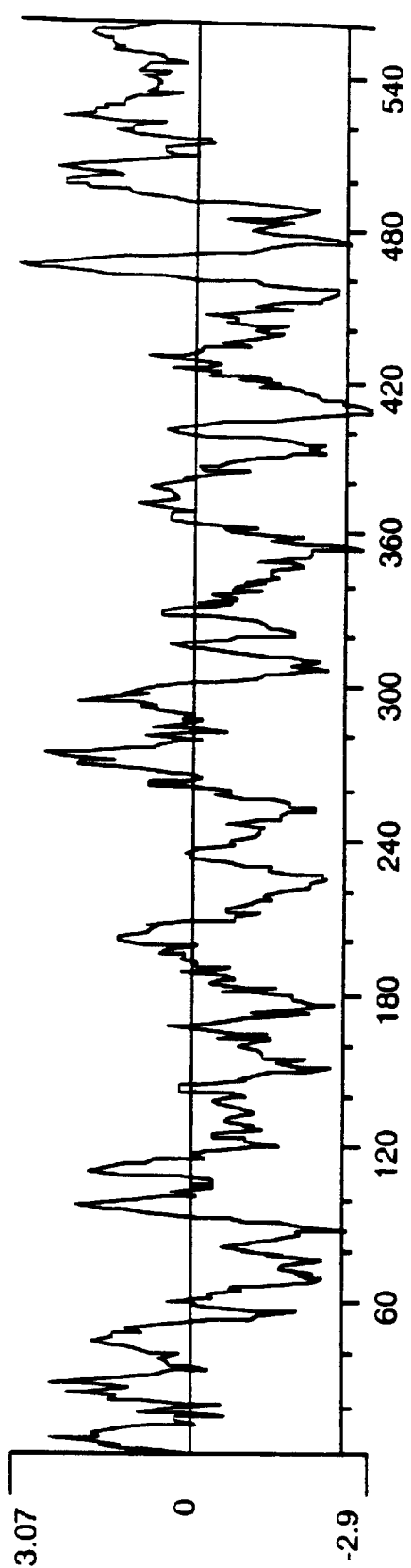

In one embodiment, the invention encompasses a polypeptide comprising the amino acid sequence of SEQ ID NO:1, as shown in FIG. 1. NAPTR is 402 amino acids in length and has chemical and structural homology with human renal sodium phosphate transport protein (GI 450532; SEQ ID NO:3) and rat brain-specific sodium-dependent inorganic phosphate cotransporter (GI 507415; SEQ ID NO:4). In particular, NAPTR, human renal sodium phosphate transport protein, and rat brain-specific sodium-dependent inorganic phosphate cotransporter share 48% and 29% identity, respectively and all three have a potential N-glycosylation sites at $N_{49}$, $N_{49}$, and $N_{92}$, respectively. As illustrated by FIGS. 3A, 3B, and 3C. NAPTR, human renal sodium phosphate transport protein, and rat brain-specific sodium-dependent inorganic phosphate cotransporter have rather similar hydrophobicity plots.

The invention also encompasses NAPTR variants. A preferred NAPTR variant is one having at least 80%, and more preferably 90%, amino acid sequence identity to the NAPTR amino acid sequence (SEQ ID NO:1). A most preferred NAPTR variant is one having at least 95% amino acid sequence identity to SEQ ID NO:1.

The invention also encompasses polynucleotides which encode NAPTR. Accordingly, any nucleic acid sequence which encodes the amino acid sequence of NAPTR can be used to generate recombinant molecules which express NAPTR. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of nucleotide sequences encoding NAPTR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NAPTR, and all such variations are to be considered as being specifically disclosed.

Although nucleotide sequences which encode NAPTR and its variants are preferably capable of hybridizing to the nucleotide sequence of the naturally occurring NAPTR under appropriately selected conditions of stringency, it may be advantageous to produce nucleotide sequences encoding NAPTR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NAPTR and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode NAPTR and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding NAPTR or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding NAPTR which are encompassed by the invention include deletions, insertions, or substitutions of different nucleotides resulting in a polynucleotide that encodes the same or a functionally equivalent NAPTR. The encoded protein may also contain deletions, insertions, or substitutions of amino acid residues which produce a silent change and result in a functionally equivalent NAPTR. Deliberate amino acid substitutions may be made on the basis of similarity in polarity, charge, solubility, hydrophobicity, hydrophilicity, and/or the amphipathic nature of the residues as long as the biological activity of NAPTR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding NAPTR. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding NAPTR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NAPTR, or fusion proteins or functional equivalents thereof, may be used in recombinant DNA molecules to direct expression of NAPTR in appropriate host cells. Due to the inherent degeneracy of the genetic code, other DNA sequences which encode substantially the same or a functionally equivalent amino acid sequence may be produced and these sequences may be used to clone and express NAPTR.

As will be understood by those of skill in the art, it may be advantageous to produce NAPTR-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter NAPTR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding NAPTR may be ligated to a heterologous sequence to encode a fusion protein. For example, to screen peptide libraries for inhibitors of NAPTR activity, it may be useful to encode a chimeric NAPTR protein that can be recognized by a commercially available antibody. A fusion protein may also be engineered to contain a cleavage site located between the NAPTR encoding sequence and the heterologous protein sequence, so that NAPTR may be cleaved and purified away from the heterologous moiety.

In another embodiment, sequences encoding NAPTR may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of NAPTR, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of NAPTR, or any part thereof, may be altered during direct synthesis and/or combined using chemical methods with sequences from other proteins, or any part thereof, to produce a variant polypeptide.

In order to express a biologically active NAPTR, the nucleotide sequences encoding NAPTR or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding NAPTR and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding NAPTR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NAPTR, vectors based on SV40 or EBV may be used with an appropriate selectable marker.

In bacterial systems, a number of expression vectors may be selected depending upon the use intended for NAPTR. For example, when large quantities of NAPTR are needed for the induction of antibodies, vectors which direct high level expression of fusion proteins that are readily purified may be used. Such vectors include, but are not limited to, the multifunctional E. coli cloning and expression vectors such as Bluescript®(Stratagene), in which the sequence encoding NAPTR may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding NAPTR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1 984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–19.6.

An insect system may also be used to express NAPTR. For example, in one such system, *Autographa californica* nuclear polyhedrosis virus (AcNPV) is used as a vector to express foreign genes in *Spodoptera frugiperda* cells or in *Trichoplusia* larvae. The sequences encoding NAPTR may be cloned into a non-essential region of the virus, such as the polyhedrin gene, and placed under control of the polyhedrin promoter. Successful insertion of NAPTR will render the polyhedrin gene inactive and produce recombinant virus lacking coat protein. The recombinant viruses may then be used to infect, for example, *S. frugiperda* cells or *Trichoplusia* larvae in which NAPTR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding NAPTR may be ligated into an adenovirus transcription/translation complex consisting of the late promoter and tripartite leader sequence. Insertion in a non-essential E1 or E3 region of the viral genome may be used to obtain a viable virus which is capable of expressing NAPTR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding NAPTR. Such signals include the ATG initiation codon and adjacent sequences. In cases where sequences encoding NAPTR, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express NAPTR may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding NAPTR is inserted within a marker gene sequence, recombinant cells containing sequences encoding NAPTR can be identified by the absence of marker gene function. Alternatively, a marker gene can be placed in tandem with a sequence encoding NAPTR under the control of a single promoter. Expression of the marker gene in response to induction or selection usually indicates expression of the tandem gene as well.

Alternatively, host cells which contain the nucleic acid sequence encoding NAPTR and express NAPTR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding NAPTR can be detected by DNA-DNA or DNA-RNA hybridization or amplification using probes or portions or fragments of polynucleotides encoding NAPTR. Nucleic acid amplification based assays involve the use of oligonucleotides or oligomers based on the sequences encoding NAPTR to detect transformants containing DNA or RNA encoding NAPTR. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of NAPTR, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NAPTR is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NAPTR include oligolabeling, nick translation, end-labeling or PCR amplification using a labeled nucleotide. Alternatively, the sequences encoding NAPTR, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding NAPTR may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode NAPTR may be designed to contain signal sequences which direct secretion of NAPTR through a prokaryotic or eukaryotic cell membrane. Other recombinant constructions may be used to join sequences encoding NAPTR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and NAPTR may be used to facilitate purification. One such expression vector provides for expression of a fusion protein containing NAPTR and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying NAPTR from the fusion protein. A discussion of vectors which contain fusion proteins is provided in Kroll, D. J. et al. (1993; DNA Cell Biol. 12:441–453).

In addition to recombinant production, fragments of NAPTR may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of NAPTR may be chemically synthesized separately and combined using chemical methods to produce the full length molecule.

Therapeutics

Based on the chemical and structural homology between NAPTR and human NPT1, NAPTR is a sodium-dependent phosphate cotransporter and appears to play a role in the regulation of phosphate levels. Increases or decreases of the level of phosphate in a subject that are above or below normal physiological values are a cause of harm to the subject.

Therefore, in one embodiment, NAPTR or a fragment or derivative thereof may be administered to a subject to treat or prevent disorders associated with decreased phosphate levels. Such disorders may include, but are not limited to cancers of the kidney, disorders of decreased phosphate levels including tumoral calcinosis, osteomalacia, osteoporosis, familial hypophosphatemia, rickets, cysteneuria, nephrocalcinosis, glomerulonephritis, renal calculus, Alzheimers disease, diabetes melitis, hereditary amyloidosis, myopathies including progressive external ophthalmoplegia, Kearns-Sayre syndrome, myoclonic epilepsy, encephalopathy, and cardiomyopathy, hypokalemia, Goodpastures' Syndrome, and disorders of cell signaling through cAMP, ATP, NADPH, and glucose-6-phosphate.

In another embodiment, a vector capable of expressing NAPTR, or a fragment or a derivative thereof, may also be administered to a subject to treat the disorders associated with decreased phosphate levels listed above.

In another embodiment, antagonists or inhibitors of NAPTR may be administered to a subject to treat or prevent disorders associated with increased phosphate levels. Such disorders may include, but are not limited to, disorders of increased phosphate levels including, hypocalciuria, hypocalcemia, and abnormal phosphate regulation in neurons, gastrointestinal tract, and liver. In one aspect, antibodies which are specific for NAPTR may be used directly as an antagonist, or indirectly as a targeting or delivery mechanism for bringing a pharmaceutical agent to cells or tissue which express NAPTR. Antibodies which are specific for NAPTR may be used directly as an antagonist, or indirectly as a targeting or delivery mechanism for bringing a pharmaceutical agent to cells or tissue which express NAPTR.

In another embodiment, a vector expressing antisense of the polynucleotide encoding NAPTR may be administered to a subject to treat or prevent the disorders associated with increased phosphate levels listed above.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of NAPTR may be produced using methods which are generally known in the art. In particular, purified NAPTR may be used to produce antibodies or to screen libraries of pharmaceutical agents to identify those which specifically bind NAPTR.

Antibodies specific to NAPTR may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with NAPTR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to NAPTR have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of NAPTR amino acids may be fused with those of another protein such as keyhole limpet hemocyanin and antibody produced against the chimeric molecule.

Monoclonal antibodies to NAPTR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce NAPTR-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for NAPTR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NAPTR and its specific antibody. A two-site, monoclonal-based immunoassay utilizing monoclonal antibodies reactive to two non-interfering NAPTR epitopes is preferred, but a competitive binding assay may also be employed (Maddox, supra).

In another embodiment of the invention, the polynucleotides encoding NAPTR, or any fragment thereof, or antisense molecules, may be used for therapeutic purposes. In one aspect, antisense to the polynucleotide encoding NAPTR may be used in situations in which it would be desirable to block the transcription of the mRNA. In particular, cells may be transformed with sequences complementary to polynucleotides encoding NAPTR. Thus, antisense molecules may be used to modulate NAPTR activity, or to achieve regulation of gene function. Such technology is now well known in the art, and sense or antisense oligomers or larger fragments, can be designed from various locations along the coding or control regions of sequences encoding NAPTR.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding NAPTR. These techniques are described both in Sambrook et al. (supra) and in Ausubel et al. (supra).

Genes encoding NAPTR can be turned off by transforming a cell or tissue with expression vectors which express high levels of a polynucleotide or fragment thereof which encodes NAPTR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding NAPTR, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NAPTR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NAPTR. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NAPTR, antibodies to NAPTR, mimetics, agonists, antagonists, or inhibitors of NAPTR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and. optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NAPTR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NAPTR or fragments thereof, antibodies of NAPTR, agonists, antagonists or inhibitors of NAPTR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind NAPTR may be used for the diagnosis of conditions or diseases characterized by expression of NAPTR, or in assays to monitor patients being treated with NAPTR, agonists, antagonists or inhibitors. The antibodies useful for diagnostic purposes may be prepared in the same manner as those described above for therapeutics. Diagnostic assays for NAPTR include methods which utilize the antibody and a label to detect NAPTR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NAPTR are known in the art and provide a basis for diagnosing altered or abnormal levels of NAPTR expression. Normal or standard values for NAPTR expression are established by combining body fluids or cell extracts taken from normal mammalian subjects, preferably human, with antibody to NAPTR under conditions suitable for complex formation The amount of standard complex formation may be quantified by various methods, but preferably by photometric, means. Quantities of NAPTR expressed in subject, control and disease, samples from biopsied tissues are compared with the standard values. Deviation between standard and subject values establishes the parameters for diagnosing disease.

In another embodiment of the invention, the polynucleotides encoding NAPTR may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of NAPTR may be correlated with disease. The diagnostic assay may be used to distinguish between absence, presence, and excess expression of NAPTR, and to monitor regulation of NAPTR levels during therapeutic intervention.

In one aspect, hybridization with PCR probes which are capable of detecting polynucleotide sequences, including genomic sequences, encoding NAPTR or closely related molecules, may be used to identify nucleic acid sequences which encode NAPTR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NAPTR, alleles, or related sequences.

Probes may also be used for the detection of related sequences, and should preferably contain at least 50% of the nucleotides from any of the NAPTR encoding sequences. The hybridization probes of the subject invention may be DNA or RNA and derived from the nucleotide sequence of SEQ ID NO:2 or from genomic sequence including promoter, enhancer elements, and introns of the naturally occurring NAPTR.

Means for producing specific hybridization probes for DNAs encoding NAPTR include the cloning of nucleic acid sequences encoding NAPTR or NAPTR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding NAPTR may be used for the diagnosis of disorders which are associated with expression of NAPTR. Examples of such disorders associated with decreased expression of NAPTR include cancers of the kidney, disorders of decreased phosphate levels including tumoral calcinosis, osteomalacia, osteoporosis, familial hypophosphatemia, rickets, cysteneuria, nephrocalcinosis, glomerulonephritis, renal calculus. Alzheimers disease, diabetes mellitus, hereditary amyloidosis, myopathies including progressive external ophthalmoplegia, Kearns-Sayre syndrome, myoclonic epilepsy, encephalopathy, and cardiomyopathy, hypokalemia, Goodpastures' Syndrome, and disorders of cell signaling through cAMP, ATP, NADPH, and glucose-6-phosphate. Examples of disorders associated with increased expression of NAPTR include abnormal phosphate regulation in neurons, gastrointestinal tract, and liver, hypocalciuria, and hypocalcemia. The polynucleotide sequences encoding NAPTR may be used in Southern or northern analysis, dot blot, or other membrane-based technologies; in PCR technologies; or in dip stick, pin, ELISA or chip assays utilizing fluids or tissues from patient biopsies to detect altered NAPTR expression. Such qualitative or quantitative methods are well known in the art.

In a particular aspect, the nucleotide sequences encoding NAPTR may be useful in assays that detect activation or induction of various cancers, particularly those mentioned above. The nucleotide sequences encoding NAPTR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NAPTR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NAPTR, a normal or standard profile for expression is established. This may be accomplished by combining body fluids or cell extracts taken from normal subjects, either animal or human, with a sequence, or a fragment thereof, which encodes NAPTR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NAPTR may involve the use of PCR. Such oligomers may be chemically synthesized, generated enzymatically, or produced from a recombinant source. Oligomers will preferably consist of two nucleotide sequences, one with sense orientation (5'–>3') and another with antisense (3'–<5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NAPTR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode NAPTR may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding NAPTR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NAPTR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NAPTR and the agent being tested, may be measured.

Another technique for drug screening which may be used provides for high throughput screening of compounds having suitable binding affinity to the protein of interest as described in published PCT application WO84/03564. In this method, as applied to NAPTR large numbers of different small test compounds are synthesized on a solid substrate, such as plastic pins or some other surface. The test compounds are reacted with NAPTR, or fragments thereof, and washed. Bound NAPTR is then detected by methods well known in the art. Purified NAPTR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NAPTR specifically compete with a test compound for binding NAPTR. In this manner, the antibodies can be used to detect the presence of any peptide which shares one or more antigenic determinants with NAPTR.

In additional embodiments, the nucleotide sequences which encode NAPTR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRAITUT02 cDNA Library Construction

The BRAITUT02 cDNA library was constructed from brain tumor tissue (specimen #0172; Mayo Clinic, Rochester Minn.). The pathology report indicated that a stage IV grade 2 renal cell carcinoma was the source of the primary tumor which had metastasized to the brain and formed an ex cerebral meningeal lesion. The patient was being treated with Decadron (Dexamethasone; Merck Sharp & Dohme, West Point Pa.) for cerebral edema/hemorrhage and with Dilantin (Phynetion; Parke-Davis. Morris Plains, N.J.) for seizures.

The frozen tissue was homogenized and lysed using a Brinkmann Homogenizer Polytron PT-3000 (Brinkmann Instruments, Westbury N.J.). The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with phenol chloroform pH 4.0, precipitated using 0.3 M sodium acetate and 2.5 volumes of ethanol, resuspended in DEPC-treated water and DNase treated at 37° C. The RNA was re-extracted with phenol chloroform pH 4.0 and precipitated using sodium acetate and ethanol as before. The RNA was then isolated using the Qiagen Oligotex kit (QIAGEN Inc; Chatsworth Calif.) and used to construct the cDNA library.

The RNA was handled according to the recommended protocols in the SuperScript Plasmid System for cDNA Synthesis and Plasmid Cloning (Cat. #18248-013; Gibco/BRL Gaithersburg MD). cDNAs were fractionated on a Sepharose CL4B column (Cat. #275105, Pharmacia), and those cDNAs exceeding 400 bp were ligated into pSport I. The plasmid pSport I was subsequently transformed into DH5a™ competent cells (Cat. #18258-012, Gibco/BRL).

II Isolation and Sequencing of cDNA Clones

Plasmid DNA was released from the cells and purified using the REAL Prep 96 Plasmid Kit (Catalog #26173 QIAGEN, Inc.). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) the cultures were incubated for 19 hours after the wells were inoculated and then lysed with 0.3 ml of lysis buffer; 3) following isopropanol precipitation, the plasmid DNA pellet was resuspended in 0.1 ml of distilled water. After the last step in the protocol, samples were transferred to a Beckman 96-well block for storage.

The cDNAs were sequenced by the method of Sanger F and AR Coulson (1975; J Mol Biol 94:441 f), using a Hamilton Micro Lab 2200 (Hamilton, Reno Nev.) in combination with Peltier Thermal Cyclers (PTC200 from MJ Research, Watertown Mass.) and Applied Biosystems 377 or 373 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding NAPTR occurs. Abundance and percent abundance are also reported. Abundance directly reflects the number of times a particular transcript is represented in a cDNA library, and percent abundance is abundance divided by the total number of sequences examined in the cDNA library.

V Extension of NAPTR to Full Length

Incyte Clone 754412.est (SEQ ID NO:5) was used to design oligonucleotide primers to extend the partial nucleotide sequence to full length. One primer was synthesized to initiate extension in the antisense direction (XLR= CTTGATGCTCCCATGAGAAAACTGG, SEQ ID NO:6), and the other was synthesized to extend sequence in the sense direction (XLF= AGGATTTTCGAGCATAGCACCTGTC, SEQ ID NO:7). PCR using these primers allowed the extension of the known partial sequence "outward" and produced three amplicons which were subsequently sequenced using the shotgun method (Messing, J., Crea, R., Seeburg, P. (1981) Nucleic Acids Res. 9:309–321).

The initial primers were designed using OLIGO® 4.06 primer analysis software (National Biosciences), or another appropriate program. Optimum primers are generally 22–30 nucleotides in length, have a GC content of 50% or more, and anneal to the target sequence at temperatures about 68°–72° C. Any stretch of nucleotides which would result in hairpin structures and primer-primer dimerizations was avoided.

Extension of Incyte Clone 754412.est (SEQ ID NO:5) to full length was accomplished in a single PCR experiment. Essential components of the experiment included a mixture of two commercial libraries, liver and leukocytes (Gibco/BRL, Gaithersburg Md.), the XL-PCR kit (Perkin Elmer), 40 pmol each of the XLF and XLR primers, and the recommended concentrations of all other components of the kit. PCR was performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7 min |
| Step 11 | Repeat step 8–10 for 12 cycles |
| Step 12 | 72° C. for 8 min |
| Step 13 | 4° C. (and holding) |

After PCR, 5–10 μl aliquot of the reaction mixture was analyzed by electrophoresis in a low concentration (about 0.6–0.8%) agarose mini-gel to determine if the sequence was extended. The bands thought to contain the largest products were selected and cut out of the gel. Further purification involved gel extraction using a method such as QIAQuick™ (QIAGEN Inc). After the DNA was recovered, Klenow enzyme was used to trim single-stranded, nucleotide overhangs creating blunt ends to facilitate religation and cloning.

The reaction products were precipitated in ethanol and redissolved in 13 µl of ligation buffer. After 1 µl T4-DNA ligase (15 units) and 1 µl T4 polynucleotide kinase were added, the mixture was incubated at room temperature for 2–3 hours or overnight at 16° C.

Competent *E. coli* cells (in 40 µl of appropriate media) were transformed with 3 µl of ligation mixture and cultured in 80 µl of SOC medium (Sambrook J et al, supra). The whole transformation mixture was incubated for one hour at 37° C. and plated on Luria Bertani (LB)-agar (Sambrook J et al, supra) containing 2×carbenicillin (2×Carb). The following day, several colonies were randomly picked from each plate and cultured in 150 µl of liquid LB/2× Carb medium placed in an individual well of a commercially-available, sterile 96-well microtiter plate. The next day, 5 µl of each overnight culture was transferred into a non-sterile 96-well plate. After being diluted 1:10 with water, 5 µl of each sample was transferred into a PCR array.

For PCR amplification, 18 µl of concentrated PCR reaction mix (3.3×) containing 4 units of rTth DNA polymerase, a vector primer and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the full length sequence of 745412 (SEQ ID NO:2) can be used to obtain 5' sequences, promoters or regulatory elements from appropriate genomic libraries.

VI Labeling and Use of Hybridization Probes

Hybridization probes derived from SEQ ID NO:2 are employed to screen cDNAs, genomic DNAs, or mRNAs. Although the labeling of oligonucleotides, consisting of about base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 ×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the NAPTR-encoding sequence, or any part thereof, is used to inhibit in vivo or in vitro expression of naturally occurring NAPTR. Although use of antisense oligonucleotides, comprising about 20 base-pairs, is specifically described, essentially the same procedure is used with larger cDNA fragments. An oligonucleotide based on the coding sequences of NAPTR, as shown in FIG. 1, is used to inhibit expression of naturally occurring NAPTR. The complementary oligonucleotide is designed from the most unique 5' sequence as shown in FIG. 1 and used either to inhibit transcription by preventing promoter binding to the upstream nontranslated sequence or translation of an NAPTR-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIG. 1.

VIII Expression of NAPTR

Expression of NAPTR is accomplished by subcloning the cDNAs into appropriate vectors and transforming the vectors into host cells. In this case, the cloning vector, pSport, previously used for the generation of the cDNA library is used to express NAPTR in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of NAPTR into the bacterial growth media which can be used directly in the following assay for activity.

IX Demonstration of NAPTR Activity

NAPTR can be assayed by injecting *Xenopus laevis* oocytes at stages V and VI with NAPTR mRNA (10 ng per oocyte) and incubating for 3 days at 18° C. in OR2 medium (82.5 mM NaCl, 2.5 mM KCL, 1 mM $CaCl_2$, 1 mM MgC12, 1 mM $Na_2HPO_4$, 5 mM Hepes, 3.8 mM NaOH, 50 ug/mi gentamycin, pH 7.8) before switching to standard uptake medium (100 mM NaCl, 2 mM KCL, 1 mM $CaCl_2$, 1 mM MgC12, 10 mM Hepes/Tris pH 7.5). Uptake of phosphate is initiated by adding 0.1 mM $KH_2PO_4$ containing 30 uCi of $^{32}$P in uptake medium and incubating for 30 minutes. Uptake is terminated by washing the oocytes three times in $Na^+$-free medium, measuring the incorporated $^{32}$P, and comparing with controls (Ni, B. (1993) supra).

X Production of NAPTR Specific Antibodies

NAPTR that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NAPTR Using Specific Antibodies

Naturally occurring or recombinant NAPTR is substantially purified by immunoaffinity chromatography using antibodies specific for NAPTR. An immunoaffinity column is constructed by covalently coupling NAPTR antibody to an activated chromatographic resin, such as CnBr-activated Sepharose (Pharmacia & Upjohn). After the coupling, the resin is blocked and washed according to the manufacturer's instructions.

Media containing NAPTR is passed over the immunoaffinity column, and the column is washed under conditions that allow the preferential absorbance of NAPTR (e.g., high ionic strength buffers in the presence of detergent). The column is eluted under conditions that disrupt antibody/NAPTR binding (eg, a buffer of pH 2–3 or a high concentration of a chaotrope, such as urea or thiocyanate ion), and NAPTR is collected.

XII Identification of Molecules Which Interact with NAPTR

NAPTR or biologically active fragments thereof are labeled with 125I Bolton-Hunter reagent (Bolton et al. (1973) Biochem. J. 133: 529). Candidate molecules previously arrayed in the wells of a multi-well plate are incubated with the labeled NAPTR, washed and any wells with labeled NAPTR complex are assayed. Data obtained using different concentrations of NAPTR are used to calculate values for the number, affinity, and association of NAPTR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polypeptide comprising the amino acid sequence of SEQ ID NO:1.

2. An isolated polypeptide of claim 1, consisting of the sequence of SEQ ID NO:1.

3. A composition comprising a polypeptide of claim 1 and a pharmaceutically acceptable excipient.

4. A composition of claim 3, wherein the polypeptide consists of the sequence of SEQ ID NO:1.

5. A method for screening a compound for effectiveness as an agonist of a polypeptide of claim 1, the method comprising:

a) exposing a sample comprising a polypeptide of claim 1 to a compound, and b) detecting agonist activity in the sample.

6. A method for screening a compound for effectiveness as an antagonist of a polypeptide of claim 1, the method comprising:

a) exposing a sample comprising a polypeptide of claim 1 to a compound, and b) detecting antagonist activity in the sample.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 401 amino acids
        (B) TYPE: amino acid
        (C) STRANDEDNESS: single
        (D) TOPOLOGY: linear (vii) IMMEDIATE SOURCE:
        (A) LIBRARY: BRAITUT02
        (B) CLONE: 754412

(xi) SEQUENCE DESCRIPTION: SEQ ID NO:1:

Met Gln Val Asp Glu Thr Leu Ile Pro Arg Lys Val Pro Ser Leu Cys
 1               5                  10                  15

Ser Ala Arg Tyr Gly Ile Ala Leu Val Leu His Phe Cys Asn Phe Thr
                20                  25                  30

Thr Ile Ala Gln Asn Val Ile Met Asn Ile Thr Met Val Ala Met Val
            35                  40                  45

Asn Ser Thr Ser Pro Gln Ser Gln Leu Asn Asp Ser Ser Glu Val Leu
    50                  55                  60

Pro Val Asp Ser Phe Gly Gly Leu Ser Lys Ala Pro Lys Ser Leu Pro
65                  70                  75                  80

Ala Lys Ser Ser Ile Leu Gly Gly Gln Phe Ala Ile Trp Glu Arg Trp
                85                  90                  95

Gly Pro Pro Gln Glu Arg Ser Arg Leu Cys Ser Ile Ala Leu Ser Gly
            100                 105                 110

Met Leu Leu Gly Cys Phe Thr Ala Ile Leu Ile Gly Gly Phe Ile Ser

```
            115                 120                 125
Glu Thr Leu Gly Trp Pro Phe Val Phe Tyr Ile Phe Gly Gly Val Gly
        130                 135                 140

Cys Val Cys Cys Leu Leu Trp Phe Val Val Ile Tyr Asp Asp Pro Val
145                 150                 155                 160

Ser Tyr Pro Trp Ile Ser Thr Ser Glu Lys Glu Tyr Ile Ile Ser Ser
                165                 170                 175

Leu Lys Gln Gln Val Gly Ser Ser Lys Gln Pro Leu Pro Ile Lys Ala
            180                 185                 190

Met Leu Arg Ser Leu Pro Ile Trp Ser Ile Cys Leu Gly Cys Phe Ser
        195                 200                 205

His Gln Trp Leu Val Ser Thr Met Val Val Tyr Ile Pro Thr Tyr Ile
    210                 215                 220

Ser Ser Val Tyr His Val Asn Ile Arg Asp Asn Gly Leu Leu Ser Ala
225                 230                 235                 240

Leu Pro Phe Ile Val Ala Trp Val Ile Gly Met Val Gly Gly Tyr Leu
                245                 250                 255

Ala Asp Phe Leu Leu Thr Lys Lys Phe Arg Leu Ile Thr Val Arg Lys
            260                 265                 270

Ile Ala Thr Ile Leu Gly Ser Leu Pro Ser Ser Ala Leu Ile Val Ser
        275                 280                 285

Leu Pro Tyr Leu Asn Ser Gly Tyr Ile Thr Ala Thr Ala Leu Leu Thr
    290                 295                 300

Leu Ser Cys Gly Leu Ser Thr Leu Cys Gln Ser Gly Ile Tyr Ile Asn
305                 310                 315                 320

Val Leu Asp Ile Ala Pro Arg Tyr Ser Ser Phe Leu Met Gly Ala Ser
                325                 330                 335

Arg Gly Phe Ser Ser Ile Ala Pro Val Ile Val Pro Thr Val Ser Gly
            340                 345                 350

Phe Leu Leu Ser Gln Asp Pro Glu Phe Gly Trp Arg Asn Val Phe Phe
        355                 360                 365

Leu Leu Phe Ala Val Asn Leu Gly Leu Leu Phe Tyr Leu Ile Phe
    370                 375                 380

Gly Glu Ala Asp Val Gln Glu Trp Ala Lys Glu Arg Lys Leu Thr Arg
385                 390                 395                 400

Leu
```

(2) INFORMATION FOR SEQ ID NO:2:

(i) SEQUENCE CHARACTERISTICS:
        (A) LENGTH: 1643 base pairs
        (B) TYPE: nucleic acid
        (C) STRANDEDNESS: single
        (D) TOPOLOGY: linear (vii) IMMEDIATE SOURCE:
        (A) LIBRARY: BRAITUT02
        (B) CLONE: 754412

(xi) SEQUENCE DESCRIPTION: SEQ ID NO:2:

```
AGAACGGTGA GGATGACCGA CGTATAGGCG AGAGCCTAGG TACGCCATGC CAGGTCACCG      60

GTCCGGCAAT TCCCGGGTCG ACCCACGCGT CCGCTTGGAG GGACGCTGGG TTCAACTTGA     120

AGCCCTTCCA CAGACATTAA GTCGGTGAAA ACCATTCACT AGGAGAGGAG AAACACAATG     180

GCCACCAAGA CAGAGTTGAG TCCCACAGCA AGGGAGAGCA AGAACGCACA AGATATGCAA     240

GTGGATGAGA CACTGATCCC CAGGAAAGTT CCAAGTTTAT GTTCTGCTCG CTATGGAATA     300
```

```
GCCCTCGTCT TACATTTCTG CAATTTCACA ACGATAGCAC AAAATGTCAT CATGAACATC      360

ACCATGGTAG CCATGGTCAA CAGCACAAGC CCTCAATCCC AGCTCAATGA TTCCTCTGAG      420

GTGCTGCCTG TTGACTCATT TGGTGGCCTA AGTAAAGCCC CAAAGAGTCT TCCTGCAAAG      480

TCCTCAATAC TTGGGGGTCA GTTTGCAATT TGGGAAAGGT GGGGCCCTCC ACAAGAACGA      540

AGCAGACTCT GCAGCATTGC TTTATCAGGA ATGTTACTGG GATGCTTTAC TGCCATCCTC      600

ATAGGTGGCT TCATTAGTGA AACCCTTGGG TGGCCCTTTG TCTTCTATAT CTTTGGAGGT      660

GTTGGCTGTG TCTGCTGCCT TCTCTGGTTT GTTGTGATTT ATGATGACCC CGTTTCCTAT      720

CCATGGATAA GCACCTCAGA AAAAGAATAC ATCATATCCT CCTTGAAACA ACAGGTCGGG      780

TCTTCTAAGC AGCCTCTTCC CATCAAAGCT ATGCTCAGAT CTCTACCCAT TTGGTCCATA      840

TGTTTAGGCT GTTTCAGCCA TCAATGGTTA GTTAGCACAA TGGTTGTATA CATACCAACT      900

TACATCAGCT CTGTGTACCA TGTTAACATC AGAGACAATG GACTTCTATC TGCCCTTCCT      960

TTTATTGTTG CCTGGGTCAT AGGCATGGTG GGAGGCTATC TGGCAGATTT CCTTCTAACC     1020

AAAAGTTTA GACTCATCAC TGTGAGGAAA ATTGCCACAA TTTTAGGAAG TCTCCCCTCT      1080

TCAGCACTCA TTGTGTCTCT GCCTTACCTC AATTCCGGCT ATATCACAGC AACTGCCTTG     1140

CTGACGCTCT CTTGCGGATT AAGCACATTG TGTCAGTCAG GGATTTATAT CAATGTCTTA     1200

GATATTGCTC CAAGGTATTC CAGTTTTCTC ATGGGAGCAT CAAGAGGATT TTCGAGCATA     1260

GCACCTGTCA TTGTACCCAC TGTCAGCGGA TTTCTTCTTA GTCAGGACCC TGAGTTTGGG     1320

TGGAGGAATG TCTTCTTCTT GCTGTTTGCC GTTAACCTGT TAGGACTACT CTTCTACCTC     1380

ATATTTGGAG AAGCAGATGT CCAAGAATGG GCTAAAGAGA GAAAACTCAC TCGTTTATGA     1440

AGTTATCCCA CCTTGGATGG AAAAGTCATT AGGCACCGTA TTGCATAAAA TAGAAGGCTT     1500

CCGTGATGAA AATACCAGTG AAAAGATTTT TTTTTCCTGT GGCTCTTTTC AATTATGAGA     1560

TCAGTTCATT ATTTTATTCA GACTTTTTTT TGAGAGAAAT GTAAGATGAA TAAAAATTCA     1620

AATAAAATGA TAACTAAGAA TGC                                            1643
```

(2) INFORMATION FOR SEQ ID NO:3:

(i) SEQUENCE CHARACTERISTICS:
        (A) LENGTH: 467 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 450532

(xi) SEQUENCE DESCRIPTION: SEQ ID NO:3:

```
Met Gln Met Asp Asn Arg Leu Pro Pro Lys Lys Val Pro Gly Phe Cys
 1               5                  10                  15

Ser Phe Arg Tyr Gly Leu Ser Phe Leu Val His Cys Cys Asn Val Ile
            20                  25                  30

Ile Thr Ala Gln Arg Ala Cys Leu Asn Leu Thr Met Val Val Met Val
        35                  40                  45

Asn Ser Thr Asp Pro His Gly Leu Pro Asn Thr Ser Thr Lys Lys Leu
    50                  55                  60

Leu Asp Asn Ile Lys Asn Pro Met Tyr Asn Trp Ser Pro Asp Ile Gln
65                  70                  75                  80

Gly Ile Ile Leu Ser Ser Thr Ser Tyr Gly Val Ile Ile Ile Gln Val
                85                  90                  95
```

```
Pro Val Gly Tyr Phe Ser Gly Ile Tyr Ser Thr Lys Lys Met Ile Gly
            100                 105                 110

Phe Ala Leu Cys Leu Ser Ser Val Leu Ser Leu Ile Pro Pro Ala
        115                 120                 125

Ala Gly Ile Gly Val Ala Trp Val Val Cys Arg Ala Val Gln Gly
        130                 135             140

Ala Ala Gln Gly Ile Val Ala Thr Ala Gln Phe Glu Ile Tyr Val Lys
145                 150                 155                 160

Trp Ala Pro Pro Leu Glu Arg Gly Arg Leu Thr Ser Met Ser Thr Ser
                165                 170                 175

Gly Phe Leu Leu Gly Pro Phe Ile Val Leu Val Thr Gly Val Ile
            180                 185                 190

Cys Glu Ser Leu Gly Trp Pro Met Val Phe Tyr Ile Phe Gly Ala Cys
        195                 200                 205

Gly Cys Ala Val Cys Leu Leu Trp Phe Val Leu Phe Tyr Asp Asp Pro
        210                 215                 220

Lys Asp His Pro Cys Ile Ser Ile Ser Glu Lys Glu Tyr Ile Thr Ser
225                 230                 235                 240

Ser Leu Val Gln Gln Val Ser Ser Arg Gln Ser Leu Pro Ile Lys
            245                 250                 255

Ala Ile Leu Lys Ser Leu Pro Val Trp Ala Ile Ser Ile Gly Ser Phe
        260                 265                 270

Thr Phe Phe Trp Ser His Asn Ile Met Thr Leu Tyr Thr Pro Met Phe
        275                 280                 285

Ile Asn Ser Met Leu His Val Asn Ile Lys Glu Asn Gly Phe Leu Ser
290                 295                 300

Ser Leu Pro Tyr Leu Phe Ala Trp Ile Cys Gly Asn Leu Ala Gly Gln
305                 310                 315                 320

Leu Ser Asp Phe Phe Leu Thr Arg Asn Ile Leu Ser Val Ile Ala Val
                325                 330                 335

Arg Lys Leu Phe Thr Ala Ala Gly Phe Leu Leu Pro Ala Ile Phe Gly
            340                 345                 350

Val Cys Leu Pro Tyr Leu Ser Ser Thr Phe Tyr Ser Ile Val Ile Phe
        355                 360                 365

Leu Ile Leu Ala Gly Ala Thr Gly Ser Phe Cys Leu Gly Gly Val Phe
        370                 375                 380

Ile Asn Gly Leu Asp Ile Ala Pro Arg Tyr Phe Gly Phe Ile Lys Ala
385                 390                 395                 400

Cys Ser Thr Leu Thr Gly Met Ile Gly Gly Leu Ile Ala Ser Thr Leu
                405                 410                 415

Thr Gly Leu Ile Leu Lys Gln Asp Pro Glu Ser Ala Trp Phe Lys Thr
            420                 425                 430

Phe Ile Leu Met Ala Ala Ile Asn Val Thr Gly Leu Ile Phe Tyr Leu
        435                 440                 445

Ile Val Ala Thr Ala Glu Ile Gln Asp Trp Ala Lys Glu Lys Gln His
        450                 455                 460

Thr Arg Leu
465

(2) INFORMATION FOR SEQ ID NO:4:

(i) SEQUENCE CHARACTERISTICS:
        (A) LENGTH: 560 amino acids
        (B) TYPE: amino acid
```

(C) STRANDEDNESS: single
          (D) TOPOLOGY: linear (vii) IMMEDIATE SOURCE:
          (A) LIBRARY: GenBank
          (B) CLONE: 507415

(xi) SEQUENCE DESCRIPTION: SEQ ID NO:4:

Met Glu Phe Arg Gln Glu Phe Arg Lys Leu Ala Gly Arg Ala Leu
 1               5                  10                  15

Gly Arg Leu His Arg Leu Leu Glu Lys Arg Gln Glu Gly Ala Glu Thr
            20                  25                  30

Leu Glu Leu Ser Ala Asp Gly Arg Pro Val Thr Thr His Thr Arg Asp
        35                  40                  45

Pro Pro Val Val Asp Cys Thr Cys Phe Gly Leu Pro Arg Arg Tyr Ile
    50                  55                  60

Ile Ala Ile Met Ser Gly Leu Gly Phe Cys Ile Ser Phe Gly Ile Arg
65                  70                  75                  80

Cys Asn Leu Gly Val Ala Ile Val Ser Met Val Asn Asn Ser Thr Thr
                85                  90                  95

His Arg Gly Gly His Val Val Gln Lys Ala Gln Phe Asn Trp Asp
            100                 105                 110

Pro Glu Thr Val Gly Leu Ile His Gly Ser Phe Phe Trp Gly Tyr Ile
        115                 120                 125

Val Thr Gln Ile Pro Gly Gly Phe Ile Cys Gln Lys Phe Ala Ala Asn
    130                 135                 140

Arg Val Phe Gly Phe Ala Ile Val Ala Thr Ser Thr Leu Asn Met Leu
145                 150                 155                 160

Ile Pro Ser Ala Ala Arg Val His Tyr Gly Cys Val Ile Phe Val Arg
                165                 170                 175

Ile Leu Gln Gly Leu Val Glu Gly Val Thr Tyr Pro Ala Cys His Gly
            180                 185                 190

Ile Trp Ser Lys Trp Ala Pro Pro Leu Glu Arg Ser Arg Leu Ala Thr
        195                 200                 205

Thr Ala Phe Cys Gly Ser Tyr Ala Gly Ala Val Val Ala Met Pro Leu
    210                 215                 220

Ala Gly Val Leu Val Gln Tyr Ser Gly Trp Ser Ser Val Phe Tyr Val
225                 230                 235                 240

Tyr Gly Ser Phe Gly Ile Phe Trp Tyr Leu Phe Trp Leu Leu Val Ser
                245                 250                 255

Tyr Glu Ser Pro Ala Leu His Pro Ser Ile Ser Glu Glu Arg Lys
            260                 265                 270

Tyr Ile Glu Asp Ala Ile Gly Glu Ser Ala Lys Leu Met Asn Pro Val
        275                 280                 285

Thr Lys Phe Asn Thr Pro Trp Arg Arg Phe Phe Thr Ser Met Pro Val
    290                 295                 300

Tyr Ala Ile Ile Val Ala Asn Phe Cys Arg Ser Trp Thr Phe Tyr Leu
305                 310                 315                 320

Leu Leu Ile Ser Gln Pro Ala Tyr Phe Glu Glu Val Phe Gly Phe Glu
                325                 330                 335

Ile Ser Lys Val Gly Leu Val Ser Ala Leu Pro His Leu Val Met Thr
            340                 345                 350

Ile Ile Val Pro Ile Gly Gly Gln Ile Ala Asp Phe Leu Arg Ser Arg
        355                 360                 365

His Ile Met Ser Thr Thr Asn Val Arg Lys Leu Met Asn Cys Gly Gly

```
           370                 375                 380
Phe Gly Met Glu Ala Thr Leu Leu Leu Val Val Gly Tyr Ser His Ser
385                 390                 395                 400

Lys Gly Val Ala Ile Ser Phe Leu Val Leu Ala Val Gly Phe Ser Gly
                405                 410                 415

Phe Ala Ile Ser Gly Phe Asn Val Asn His Leu Asp Ile Ala Pro Arg
                420                 425                 430

Tyr Ala Ser Ile Leu Met Gly Ile Ser Asn Gly Val Gly Thr Leu Ser
                435                 440                 445

Gly Met Val Cys Pro Ile Ile Val Gly Ala Met Thr Lys His Lys Thr
            450                 455                 460

Arg Glu Glu Trp Gln Tyr Val Phe Leu Ile Ala Ser Leu Val His Tyr
465                 470                 475                 480

Gly Gly Val Ile Phe Tyr Gly Val Phe Ala Ser Gly Glu Lys Gln Pro
                485                 490                 495

Trp Ala Glu Pro Glu Glu Met Ser Glu Glu Lys Cys Gly Phe Val Gly
                500                 505                 510

His Asp Gln Leu Ala Gly Ser Asp Glu Ser Glu Met Glu Asp Glu Val
            515                 520                 525

Glu Pro Pro Gly Ala Pro Pro Ala Pro Pro Pro Ser Tyr Gly Ala Thr
        530                 535                 540

His Ser Thr Val Gln Pro Pro Arg Pro Pro Pro Val Arg Asp Tyr
545                 550                 555                 560
```

(2) INFORMATION FOR SEQ ID NO:5:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (vii) IMMEDIATE SOURCE:
        (A) LIBRARY: BRAITUT02
        (B) CLONE: 754412

(xi) SEQUENCE DESCRIPTION: SEQ ID NO:5:

```
ATTTATATCA ATGTCTTAGA TATTGCTCCA AGGTATTCCA GTTTTCTCAT GGGAGCATCA    60

AGAGGATTTT CGAGCATAGC ACCTGTCATT GTACCCACTG TCAGTGGATT TCTTCTTAGT   120

CAGGACCCTG AGTTTGGGTG GAGGAATGTC TTCTTCTTGC TGTTTGCCGT TAACCTGTTA   180

GGACTACTCT TCTACCTCAT ATTTGGAGAA GCAGATGTCC AAGAATGGGC TAAAGAGAGA   240

AAACTCACTC GTTTATGAAG TTATCCCACC TT                                 272
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: XLR (xi) SEQUENCE DESCRIPTION: SEQ ID NO:6:

```
CTTGATGCTC CCATGAGAAA ACTGG                                          25
```

(2) INFORMATION FOR SEQ ID NO:7:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: XLF (xi) SEQUENCE DESCRIPTION: SEQ ID NO:7:

AGGATTTTCG AGCATAGCAC CTGTC                                              25
```